United States Patent [19]

Mickle, deceased et al.

[11] 4,183,966

[45] Jan. 15, 1980

[54] METHOD OF MANUFACTURING A HIGH PROTEIN SNACK FOOD

[75] Inventors: James B. Mickle, deceased, late of Stillwater, Okla., by Lois T. Mickle, widow and legally appointed agent of the executor; Wanda J. Smith, Stillwater; Laurel M. Dieken, Tulsa, both of Okla.

[73] Assignee: The Board of Regents of the Oklahoma Agricultural & Mechanical Colleges acting for and on behalf of Oklahoma State University of Agriculture and Applied Science, Stillwater, Okla.

[21] Appl. No.: 896,348

[22] Filed: Apr. 14, 1978

[51] Int. Cl.$^2$ .............................. A23J 1/18; A23J 1/20
[52] U.S. Cl. ....................................... 426/42; 426/243; 426/551; 426/558; 426/560; 426/657; 426/438; 426/439; 426/808
[58] Field of Search ............... 426/41, 42, 43, 241, 426/242, 243, 551, 558, 559, 560, 657, 438, 439, 808, 656, 583

[56] References Cited

U.S. PATENT DOCUMENTS

| | | | |
|---|---|---|---|
| 2,809,113 | 10/1957 | Stimpson et al. | 426/42 X |
| 3,282,701 | 11/1966 | Wong et al. | 426/560 X |
| 3,348,950 | 10/1967 | Weiss | 426/808 X |
| 3,849,582 | 11/1974 | Blagdon et al. | 426/808 X |
| 3,911,142 | 10/1975 | Huelskamp et al. | 426/808 X |
| 4,055,666 | 10/1977 | Jeffreys et al. | 426/41 X |

OTHER PUBLICATIONS

Food Engineering, Aug. 1964, p. 95.

*Primary Examiner*—Raymond N. Jones
*Assistant Examiner*—Ester M. Kepplinger
*Attorney, Agent, or Firm*—Head & Johnson

[57] ABSTRACT

A method of manufacturing a high protein snack food including the steps of inoculating whey, such as derived from cheese making, with yeast, incubating the mixture with aeration until substantially all the whey lactose is utilized by the yeast, heating the culture to precipitate the whey protein, separating the whey protein and yeast cells to provide a paste-like material, mixing the whey protein and yeast cell paste with a filler composed of potato flakes or corn starch or a mixture of the two, plus either baking powder or baking soda (to reduce acidity), plus salt, and egg whites, into a dough, extruding the dough to provide snack-like pieces, frying the pieces in a deep fat fryer, and then cooking the fried pieces in a microwave oven.

5 Claims, 1 Drawing Figure

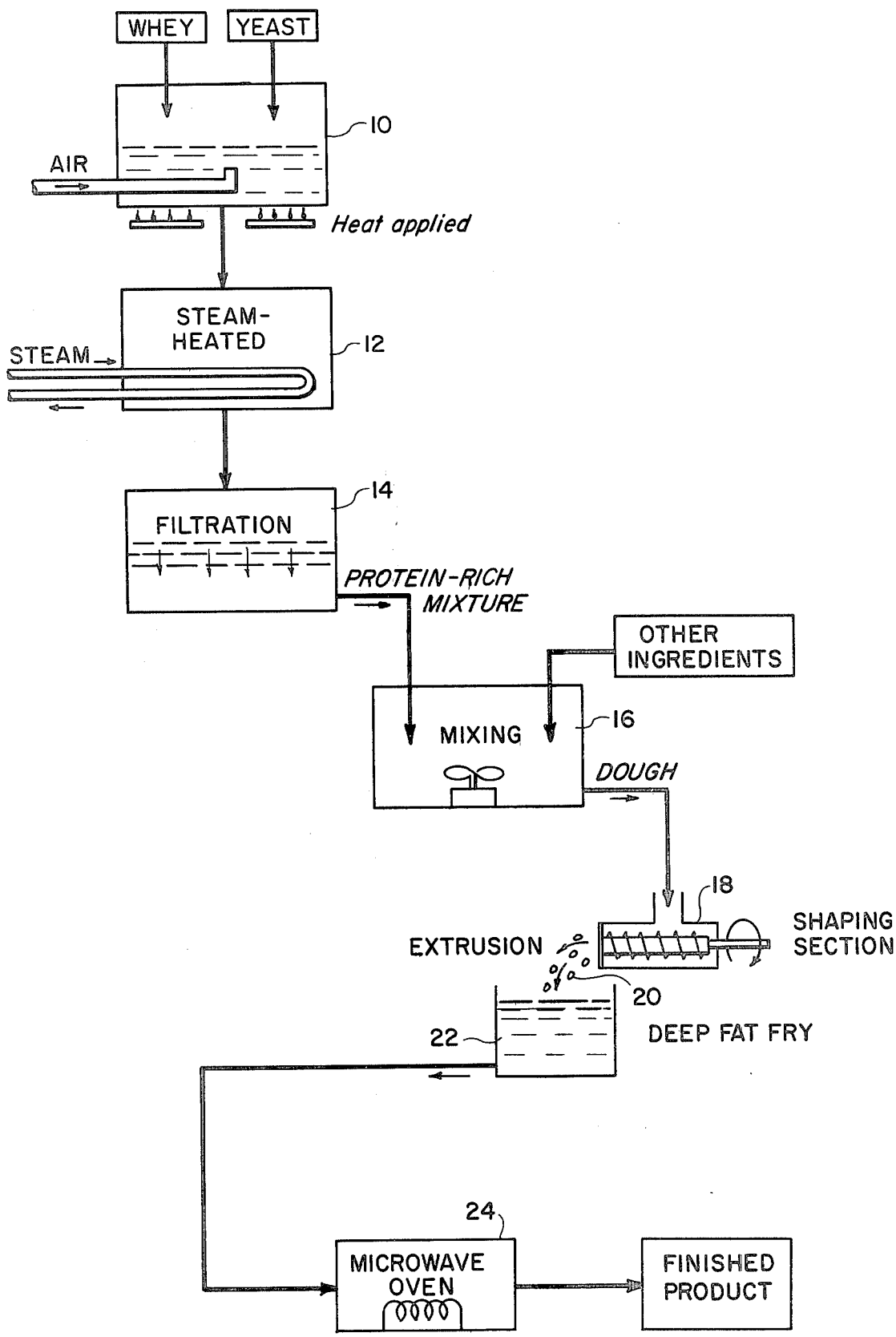

METHOD OF MANUFACTURING A HIGH PROTEIN SNACK FOOD

BACKGROUND AND OBJECTS OF THE INVENTION

In the United States and many other countries of the world, snack-type foods have become exceedingly popular. By "snack-type foods" is meant crisp fried foods which are adaptable to be eaten from the hand and which are easily preserved and transported. Such snack-type foods include potato chips and other chip-like products made of corn, wheat, potatoes, and other grain materials.

Typically, the snack-like foods are of a vegetable or grain mixture and are shaped into the desired pieces and then deep fried to produce a product which is convenient and ready to eat.

One deleterious characteristic of most existing snack-type foods is that they are characteristically high in sugar and starches and low in protein. Typically, the ready-to-eat snack-type foods may contain 50 to 70% by weight of starch and sugars and only 6 to 10% protein. For this reason many dietary authorities have recommended against the excess use of snack-type foods, and this is particularly true as to the diet of average American teenagers, who are great consumers of snack foods.

The present invention is directed towards providing a snack-type food similar to potato chips and corn chips and the many other varieties presently on the market but in a composition which provides two to three times as much protein and only ⅓ to ½ as much sugar and starch. Stated another way, and object of this invention is to provide a snack-type food which has the appearance, crispiness, taste, and convenience of typical snack-type foods presently marketed but which has superior dietary characteristics due to increased protein and decreased starch composition.

Another object of this invention is to provide a snack-type crisp convenient food which uses as its basic raw material the whey left as a waste product from the manufacture of cottage cheese and other type cheeses by the dairy industry.

These general objects, as well as other and more specific objects of the invention will be fulfilled in the following description and claims, taken in conjunction with the attached drawings.

DESCRIPTION OF THE DRAWING

The drawing illustrates the sequence of steps utilized in the practice of the invention wherein whey is utilized as a raw material for the production of a finished snack-type product comparable to the products on today's market but higher in protein and lower in carbohydrates.

SUMMARY OF THE INVENTION

A method of manufacturing a high protein snack food including the steps of inoculating when with *Kluyveromyces fragilis* yeast, incubating the mixture under continuous aeration at about 35° C. until substantially all of the whey lactose has been consumed by the yeast, heating the cultured whey to precipitate out the whey protein, recovering the precipitated whey by means of filtration, gravity separation, or centrifugation to provide whey protein paste, mixing the whey protein paste with egg white, salt, leavening, and a filler of dehydrated potato flakes and corn starch, shaping the mixture into a preselected configuration to provide snack-like pieces, frying the pieces in a deep fat cooker, and subsequently cooking the fried pieces in a microwave oven to complete the cooking so that the completed pieces have a degree of crispness desired.

DETAILED DESCRIPTION OF THE PREFERRED EMBODIMENT

The basic raw material of the food product of this invention is whey. Whey is the serum or watery part of milk containing sugar, minerals, and lactalbumin that is separated from the thicker or more coagulable curds in the process of making cheese, and particularly the type cheese commonly referred to as "cottage cheese". In many cheese-making plants the whey is a waste product, and in some instances is one of the dairy industry's major waste disposal problems. Whey is utilized in the present method to provide a high protein snack-like food comparable in taste, appearance, and convenience to existing snack-like foods prepared from potatoes and grain products currently marketed.

Referring to the drawing, the first step in the production of the food product is to inoculate whey with yeast; that is, *Kluyveromyces fragilis*, in a vented vat 10. In the incubation step, the inoculated whey is maintained at approximately 35° C. with continuous aeration. The whey requires no additional nutrients. The incubation is continued until all of the whey sugar, or lactose, has been utilized by the yeast. While the length of time required may vary according to conditions, including the quality of the whey, the exact temperature conditions, the amount of aeration and so forth, the required time to fully incubate the mixture to allow the full utilization by the yeast growth to consume substantially all of the whey lactose requires about 16 to 24 hours.

The cultured mixture is next heated by injecting steam in a precipitator 12 to about 89° C. to 91° C. to cause the whey protein to precipitate. It can be seen that the step of precipitation may be carried out in the incubation vat 10 rather than in a separate precipitator vessel 12 and the exact structure utilized to practice these steps is a matter of choice and not a part of the present invention.

After the whey protein has been precipitated, the mixture is cooled, and the whey proteins and yeast cells are recovered in filter 14. The filtration step represented may be carried out in a variety of ways. One way is to allow the whey protein and yeast cells to separate by gravity, and in such instances this step can be carried out in the precipitator 12 or the whole process to this point in the method can be carried out in a single vessel indicated by vat 10. As an alternative, the water may be removed; that is, the whey protein and yeast cells extracted, by means of centrifugation or by various filtration apparatuses, all of which are well known to practitioners in the dairy processing art. Regardless of the specific means of separating water and other moisture content from the precipitated whey protein, the result of such separation emanating from the apparatus indicated by filter 14, is a protein rich mixture in the form of a sludge or paste.

The sludge or paste is conveyed to a mixer 16 where it is combined with other ingredients, including potato flakes, baking powder or baking soda, salt, egg white and corn starch. In essence, it may be said that there are four other ingredients; that is (1) salt (NaCl); (2) egg white; (3) a leavening agent, which may be either baking powder or baking soda, or a combination of the two; and (4) a filler which is potato flakes and corn starch.

The combined ingredients are stirred in the mixer 16 into a dough which is passed to an extruder 18. Here the dough is extruded or otherwise formed by machinery into preselected shapes and sizes of pieces. In another method of operating the extruder 18 the pieces may extrude in the form of flat ribbons which break into random lengths such as the type of snack foods presently marketed. The selection of the type of extruder 18 and the size and shape of the pieces of dough 20, will depend upon the personal preference of the manufacturer. Machinery is readily available for producing a variety of different shapes and sizes of pieces 20.

The pieces 20 are then deposited in a deep fat fryer 22. The oil utilized in the deep fat fryer 22 is maintained at about 204° as a preferred temperature, and the pieces 20 are cooked in the deep fat fryer for about 15 seconds to cook and brown them. Obviously, if a lower temperature fat is utilized, a longer time is required, and if a higher temperature is utilized, a shorter time is required. The thickness or bulk of the pieces will vary the required cooking time somewhat. The combination of an oil temperature of 204° and a cooking time of 15 seconds is preferred as a result of experimentation to produce the finished pieces which are of the best taste and appearance appeal. The flavor and other characteristics of the finished product will depend to some extent upon the type of oil that is used. An oil that is liquid at room temperature is preferred.

The fried pieces from fryer 22 are conveyed to a microwave oven 24. Here the fried pieces are cooked by microwave action for approximately 2 to 3 minutes. This is sufficient time to complete the cooking of the pieces to final completeness.

While the variety of ingredients which are placed in mixer 16 may vary, a typical recipe is as follows:

| Ingredient | % by Weight |
|---|---|
| Yeast-Whey Protein | 70–80 (depending on water content |
| Cornstarch | ¾–1 |
| Egg White | ½–¾ |
| Salt (NaCl) | 1–2 |
| Baking Powder or Baking Soda | 1½–2½ |
| Potato Flakes (dehydrated) | 15–20 (depending on water content of yeast-whey) |

The material referred to as "filler" in the description of the process is preferably formed of dehydrated potato flakes which may be partially replaced by corn starch so that the total quantity of these two ingredients mentioned in the typical recipe above may remain the same although the ratio of these two ingredients may vary. The amount of corn starch and potato flakes selected or interchanged depends on the flavor desired in the final product.

The output of mixer 16 should be a dough which has the texture and consistency of pie crust dough. The final dough should feel moist to the hand, but stick together when rolled, much as does a pie crust or bread dough.

When the typical recipe above is used, the approximate composition of the dough and final product compared to two convenience food products presently on the market is illustrated in the following table:

| Ingredient | Product Dough | Final | Chippos | Crisp-i-taters |
|---|---|---|---|---|
| Water | 60–70 | 3–5 | 3 | 4–5 |
| Protein | 11–19 | 18–19 | 7 | 6 |
| Fat | 0 | 13–17 | 17 | 31–31½ |
| Ash (minerals) | 3 | 6–7 | 4–5 | 3–4 |
| Sugar and Starch | 14–20 | 28–40 | 68 | 55 |
| Fiber & other long chain carbohydrates | 2–9 | 14–20 | — | — |

"Chippos" and "Crisp-i-taters" are trademarks of snack-type foods presently manufactured by General Mills Company. The comparison of the ingredients in the finished product of this invention with the existing snack-type products illustrates the higher percentage of protein and reduced percentage of carbohydrates in the finished product. The greatly increased nutritional advantage of the product of this invention is dramatically illustrated, and at the same time it is emphasized that the product is manufactured utilizing whey, a material which is frequently considered a waste product of the dairy industry and which has, in some instances, been a major waste disposal problem.

While the invention has been described in certain detail, it is understood that it is not limited to the embodiment set forth herein for purposes of exemplification, but is to be limited only by the scope of the attached claim or claims, including the full range of equivalency to which each element thereof is entitled.

What is claimed is:
1. A method of manufacturing a high protein snack food comprising:
   a. inoculating whey with *Kluyveromyces fragilis* yeast;
   b. incubating the mixture under continuous aeration at about 35° C. until substantially all the whey lactose has been utilized by the yeast;
   c. heating the cultured whey to about 89° C. to precipitate the whey protein;
   d. recovering the precipitated whey protein under moisture removal conditions to form a whey protein paste;
   e. mixing the whey protein paste with egg whites, salt, a leavening agent selected from the group consisting of baking powder and baking soda, and a filler selected from the group consisting of dehydrated potato flakes, corn starch, and mixtures thereof;
   f. shaping the mixture of step (e) into snack-like pieces;
   g. frying the pieces in deep fat; and
   h. cooking the fried pieces in a microwave oven to complete the cooking to a selected level of crispness.

2. A method of manufacturing a high protein snack food according to claim 1 wherein step (b) includes incubating the mixture under continuous aeration of about 35° C. for about 16 to 24 hours.

3. A method of manufacturing a high protein snack food according to claim 1 wherein step (e) includes mixing the whey protein paste with other ingredients in about the following percentage by weight:
   Yeast whey protein: 70–80
   Egg white: ½–¾
   Salt (NaCl): 1–2
   Leavening agent: 1½–2½
   Filler: 15–20

4. A method of manufacturing a high protein snack food according to claim 1 wherein step (g) includes frying the pieces in deep fat at about 204° C. for about 15 seconds.

5. A method of manufacturing a high protein snack food according to claim 1 wherein step (g) includes frying the pieces in deep fat at about 204° C. for about 15 seconds and step (h) includes cooking the pieces in a microwave oven for about 2 to 3 minutes.

* * * * *